(12) United States Patent
Ohashi et al.

(10) Patent No.: US 11,793,720 B2
(45) Date of Patent: Oct. 24, 2023

(54) MEDICAL BAG HANGER AND BLOOD COLLECTION DEVICE PACKAGE

(71) Applicant: TERUMO KABUSHIKI KAISHA, Tokyo (JP)

(72) Inventors: Hirotaka Ohashi, Tokyo (JP); Tomonori Ijiri, Tokyo (JP); Manami Iwabuchi, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 306 days.

(21) Appl. No.: 16/073,007

(22) PCT Filed: Jan. 26, 2017

(86) PCT No.: PCT/JP2017/002626
§ 371 (c)(1),
(2) Date: Jul. 26, 2018

(87) PCT Pub. No.: WO2017/131060
PCT Pub. Date: Aug. 3, 2017

(65) Prior Publication Data
US 2019/0021948 A1    Jan. 24, 2019

(30) Foreign Application Priority Data
Jan. 29, 2016    (JP) ................. 2016-015003

(51) Int. Cl.
*A61J 1/14*    (2023.01)
*A61J 1/16*    (2023.01)
(Continued)

(52) U.S. Cl.
CPC .............. *A61J 1/1462* (2013.01); *A61J 1/16* (2013.01); *A61M 1/0209* (2013.01);
(Continued)

(58) Field of Classification Search
CPC ...... A61M 2209/082; A61M 2209/084; A61M 2209/08; A61M 5/1407; A61M 5/1414; A61M 5/1415; A61M 5/1417
See application file for complete search history.

(56) References Cited

U.S. PATENT DOCUMENTS 3,977,567 A    8/1976  Rudd
4,610,781 A *  9/1986  Bilstad ................ A61M 1/3496
                                                    210/321.65
(Continued)

FOREIGN PATENT DOCUMENTS

CN    201743999 U    2/2011
CN    103690249 A    4/2014
(Continued)

OTHER PUBLICATIONS

English Translation of Abstract and Specification of Hirotaka (JP 2012-029900). (Year: 2012).*
(Continued)

*Primary Examiner* — Ariana Zimbouski
(74) *Attorney, Agent, or Firm* — Sheridan Ross P.C.

(57) ABSTRACT

Provided is a medical bag hanger that hangs a plurality of bags of a blood sampling line set. The medical bag hanger includes a hanger main body that is hangable on a blood component separation device. The hanger main body includes a hook unit on which the plurality of bags is hooked, and a base plate on the surface of which the plurality of bags of the blood sampling line set are arranged side by side.

19 Claims, 12 Drawing Sheets

(51) Int. Cl.
  *A61M 5/14* (2006.01)
  *A61M 1/02* (2006.01)
  *A61M 1/36* (2006.01)
  *A61M 1/38* (2006.01)

(52) U.S. Cl.
  CPC ............ *A61M 1/3693* (2013.01); *A61M 5/14* (2013.01); *A61M 1/38* (2013.01); *A61M 2202/0427* (2013.01); *A61M 2205/12* (2013.01); *A61M 2205/123* (2013.01); *A61M 2209/06* (2013.01); *A61M 2209/08* (2013.01)

(56) References Cited

U.S. PATENT DOCUMENTS

| | | | | |
|---|---|---|---|---|
| 5,523,004 | A * | 6/1996 | Tanokura | A61M 1/0209 210/749 |
| 6,027,657 | A * | 2/2000 | Min | A61M 1/3693 210/782 |
| 6,390,311 | B1 * | 5/2002 | Belokin | A61M 5/1415 211/189 |
| 7,708,710 | B2 * | 5/2010 | Min | A61M 1/38 604/6.01 |
| 8,523,750 | B2 | 9/2013 | Pittinger et al. | |
| 2006/0226090 | A1 * | 10/2006 | Robinson | A61M 1/3693 210/787 |
| 2006/0265246 | A1 * | 11/2006 | Hoag | G16H 40/60 705/2 |
| 2007/0209708 | A1 * | 9/2007 | Hermann | A61M 1/0277 137/255 |
| 2009/0134284 | A1 * | 5/2009 | Chevallet | A61M 5/1415 248/95 |
| 2014/0209550 | A1 * | 7/2014 | Pryor | A61M 5/1417 211/85.13 |
| 2015/0113919 | A1 * | 4/2015 | Provitera | B65B 7/02 53/440 |

FOREIGN PATENT DOCUMENTS

| | | |
|---|---|---|
| CN | 204337400 U | 5/2015 |
| JP | 04309362 | 10/1992 |
| JP | 3466180 P | 11/2003 |
| JP | 2008-000318 | 1/2008 |
| JP | 2012-029900 | 2/2012 |
| WO | 2005/067863 A1 | 7/2005 |
| WO | 2013/099946 A1 | 7/2013 |

OTHER PUBLICATIONS

European Search Report, European Patent Application No. 17744290.0, dated Jul. 30, 2019, 13 pages.

State Intellectual Property Office of People's Republic of China, First Office Action, CN2017800081716.3, dated Jul. 28, 2020, 24 pages including English translation.

* cited by examiner

MEDICAL BAG HANGER AND BLOOD COLLECTION DEVICE PACKAGE

TECHNICAL FIELD

The present invention relates to a medical bag hanger and a blood sampling device package.

BACKGROUND ART

In recent blood donation, blood component sampling (apheresis) which eases the burden on the body of a donor is practiced in addition to whole blood sampling for taking whole blood from a donor. Blood component sampling is a blood sampling method in which a blood component sampling system (apheresis system) is used to take a specific blood component from whole blood and return the remaining components to the body of a donor.

JP 2013-514863 A discloses a blood component sampling system configured to sample blood platelets by centrifugation of whole blood taken from a donor. This blood component sampling system is provided with a blood sampling line set forming a line through which a to-be-treated blood or blood component flows, and a centrifugal device (blood component separation device) on which the blood sampling line set is mounted. The blood sampling line set includes, for example, a band-like channel through which whole blood flows in and out, and a plurality of hangable bags configured to store sampled blood components or the like. In use, the channel is mounted on a rotor of the centrifugal device, and the plurality of bags is hung on a plurality of hooks provided in the centrifugal device.

SUMMARY OF INVENTION

In the aforementioned conventional blood sampling line set, the plurality of bags including a blood component sampling bag and the like needs to be individually hung one by one on the hooks provided in the centrifugal device. In addition, the hooks for hanging the bags are provided at high positions on the back of the centrifugal device so that it is not easy for a short worker to detach the bags from the centrifugal device.

The present invention has been made in light of such problems, and an object of the present invention is to provide a medical bag hanger and a blood sampling device package which simplify attachment of a plurality of bags in a blood sampling line set to a blood component separation device.

In order to achieve the above object, the present invention provides a medical bag hanger configured to hang a plurality of bags of a blood sampling line set including the plurality of bags that is hangable, the medical bag hanger includes: a hanger main body that is hangable on a blood component separation device; and a hook unit provided on the hanger main body and having the plurality of bags hooked thereon, the hanger main body includes a base plate provided with the hook unit, and the plurality of bags is arranged side by side on a surface of the base plate.

According to the medical bag hanger of the present invention that employs the aforementioned configuration, the plurality of bags included in the blood sampling line set is assembled in advance so that, in use, the plurality of bags is easily attached to the blood component separation device with simple operation of hanging the medical bag hanger as it is on the blood component separation device. In addition, a hook for hanging the medical bag hanger is provided in the blood component separation device within arm's reach of a small worker so that the worker is able to detach the medical bag hanger without difficulty. Inside the package that houses the blood sampling line set, the tubes and the like in the blood sampling line set are housed in the back of the base plate so that the bags are prevented from being tracked by the tubes and the like.

In the medical bag hanger, the hook unit may be provided on an upper surface of the base plate, the hanger main body may further include a cover that covers the upper surface of the base plate and the hook unit in an initial state, and the cover allows the plurality of bags to be detached from the hook unit when being opened.

With this configuration, the cover is closed in the initial state so that the bags do not unintentionally come off the hanger main body when the medical bag hanger is hung on the blood component separation device. Furthermore, after blood treatment, when the cover is opened, the hook unit is exposed so that the plurality of bags is easily detachable from the hanger main body.

In the medical bag hanger, the hook unit may include a plurality of hooks on which the plurality of bags is hooked, respectively, and from which the plurality of bags is individually detached.

This configuration makes it easier to handle the plurality of bags after blood sampling.

In the medical bag hanger, the blood sampling line set may include a plurality of tubes connected to the plurality of bags, respectively, and the hanger main body may include a hook configured to fasten the plurality of tubes in a bundle.

With this configuration, a plurality of tubes is assembled so that other parts of the blood sampling line set are easily attached.

Furthermore, the present invention includes: a blood sampling line set including a plurality of bags; a medical bag hanger to which the plurality of bags is attached; and a package main body that houses the blood sampling line set and the medical bag hanger, and the medical bag hanger is the medical bag hanger according to any of the aforementioned medical bag hangers.

According to the blood sampling device package of the present invention that employs such a configuration, the plurality of bags is easily attached to the blood component separation device with simple operation of taking out the medical bag hanger from the package main body and hanging the medical bag hanger on the blood component separation device.

In the blood sampling device package, the blood sampling line set includes a cassette connected to the plurality of bags through the plurality of tubes; and a channel connected the cassette through a fluid delivery line and configured to allow blood to flow in and out, and the package main body includes a chassis having a box-like shape and provided with a bottom wall and a peripheral wall; and a lid member joined to an upper end of the peripheral wall of the chassis, and the medical bag hanger is placed on the cassette and the channel inside the package main body.

With this configuration, when taking out the blood sampling line set from the package main body, the medical bag hanger to which the plurality of bags is attached is taken out as a first step, then, the cassette is taken out as a second step, and the channel is taken out as a third step. Accordingly, the attachment procedure is easy to follow, which enables a worker to attach the blood sampling line set to the blood component separation device more easily. Particularly, when the blood sampling device package is placed on the main body of the blood component separation device and the blood sampling device package is opened on the main body to take out the blood sampling line set, following the aforementioned procedure makes it possible to attach the blood sampling line set to the blood component separation device smoothly.

In the blood sampling device package, the medical bag hanger may be foldable and housed inside the package main body as being folded.

With this configuration, even when the size of the medical bag hanger is large, it is possible to downsize the blood sampling device package.

In the blood sampling device package, the package main body may be hookable and hangable on a side surface of the blood component separation device.

With this configuration, the blood sampling device package is prepared in a space-saving manner within arm's reach of a worker.

In the blood sampling device package, the package main body may include a bag unit that houses the blood sampling line set, the bag unit includes a plurality of housing rooms communicating with each other through an opening, and components of the blood sampling line set are separately housed in the plurality of housing rooms.

With this configuration, when attaching the blood sampling line set to the blood component separation device, the components of the blood sampling line set are taken in order out of the plurality of housing rooms of the bag unit, leading to efficient attachment operation.

In the blood sampling device package, the bag unit includes a bag main body provided with the opening in a front wall of the bag unit; and a cover sheet member that covers the opening, at least a part of the cover sheet member being peelably attached to the front wall of the bag main body, and the plurality of housing rooms includes a first housing room formed between the front wall of the bag main body and the cover sheet member; and a second housing room formed inside the bag main body.

With this configuration, at first, at least a part of the cover sheet member is peeled off the bag main body so that a part of the blood sampling line set is taken out of the first housing room, and then, the remaining components of the blood sampling line set are taken out of the second housing room through the opening. Therefore, the blood sampling device package has a simple configuration so that the blood sampling line set is easily taken out.

In the blood sampling device package, the blood sampling line set may include the cassette connected to the plurality of bags through the plurality of tubes; the channel connected to the cassette through the fluid delivery line; and a blood sampling needle connected to the cassette, the medical bag hanger to which the plurality of bags is attached is housed in the first housing room, the cassette, the channel, and the blood sampling needle are housed in the second housing room, and the cassette is housed in front of the channel and the blood sampling needle in the second housing room.

With this configuration, when taking the blood sampling line set out of the bag unit, the medical bag hanger is taken out of the first housing room as a first step, the cassette is taken out of the front side of the second housing room as a second step, and then, the channel and the blood sampling needle are taken out of the second housing room as a third step. Accordingly, the attachment procedure is easy to follow, which enables a worker to attach the blood sampling line set to the blood component separation device more easily.

According to the medical bag hanger and the blood sampling device package of the present invention, a plurality of bags in the blood sampling line set is easily attached to the blood component separation device.

DESCRIPTION OF EMBODIMENTS

Several preferred embodiments of a medical bag hanger and a blood sampling device package according to the present invention will hereinafter be described with reference to the accompanying drawings.

Figure 1:
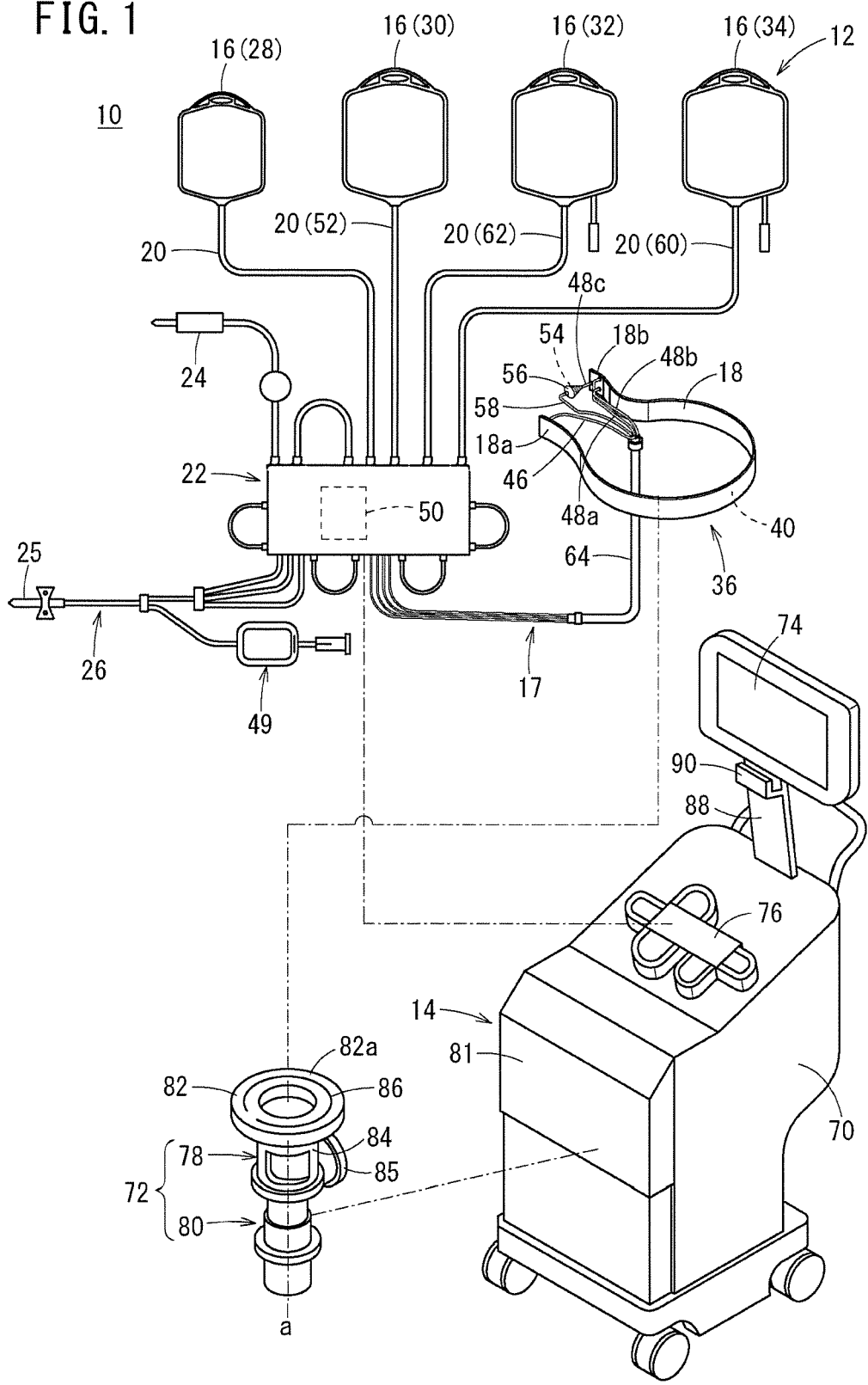
FIG. 1 is a schematic view of a blood sampling system.

In FIG. 1, a blood sampling system 10 is configured as a blood apheresis system that continuously takes blood (whole blood) from a donor and centrifuges the blood in vitro so as to sample a specific blood component (platelet in this embodiment) and returns the remaining blood components to the donor. With appropriate modification, the blood sampling system 10 is also applicable to a system for sampling whole blood.

First, the blood sampling system 10 illustrated in FIG. 1 will be described schematically. The blood sampling system 10 includes a blood sampling line set 12 configured to store and flow blood components, and a centrifugal device 14 configured to apply centrifugal force to the blood sampling line set 12. The blood sampling line set 12 includes a channel 18 serving as a primary separator into which whole blood taken from a donor is introduced and which centrifugally separates the whole blood into a plurality of blood components.

The centrifugal device 14 includes a rotor 78 configured to apply centrifugal force to the channel 18. An upper surface 82a of the rotor 78 is formed with a mounting groove 86 that extends in a circumferential direction centering on a rotation axis a of the rotor 78, and the channel 18 is mountable on the mounting groove 86. Hereinafter, the blood sampling line set 12 and the centrifugal device 14 will be described in detail.

From the aspect of contamination control and good hygiene, the blood sampling line set 12 is for one-time use. The blood sampling line set 12 includes a blood sampling/blood returning unit 26 provided with a blood sampling needle 25, an anticoagulant introduction unit 24, the channel 18, a plurality of bags 16, and a cassette 22 connected to these members.

The channel 18 is connected to the cassette 22 through a fluid delivery line 17. Meanwhile, the plurality of bags 16 is connected to the cassette 22 through a plurality of tubes 20. The plurality of bags 16 includes an auxiliary bag 28, a bag for PPP 30, a bag for platelet additive solution 32, and a bag for platelet 34.

The channel 18 is a belt-like bag which is mounted on the mounting groove 86 provided in the rotor 78 of the centrifugal device 14. Blood is introduced into the channel 18, and the channel 18 allows the blood to flow through and out of the channel 18. Furthermore, the channel 18 is a flexible bag internally including a first chamber 40 (blood separation unit) to which the whole blood of the donor is supplied, and the channel 18 is easily bent, folded, or balled up. The first chamber 40 extends from one end 18*a* of the channel 18 to the other end 18*b*. In a centrifugal process, the whole blood introduced into the first chamber 40 is separated by centrifugal force while flowing from one end 18*a* to the other end 18*b*.

An introduction tube 46 is connected to one end 18*a* of the channel 18. The introduction tube 46 is connected to the blood sampling/blood returning unit 26, involving the cassette 22. A sampling unit 49 for sampling an initial flow blood from the donor is connected to the blood sampling/blood returning unit 26. In addition, the blood sampling/blood returning unit 26 is connected to the anticoagulant introduction unit 24, involving the cassette 22.

Figure 3:
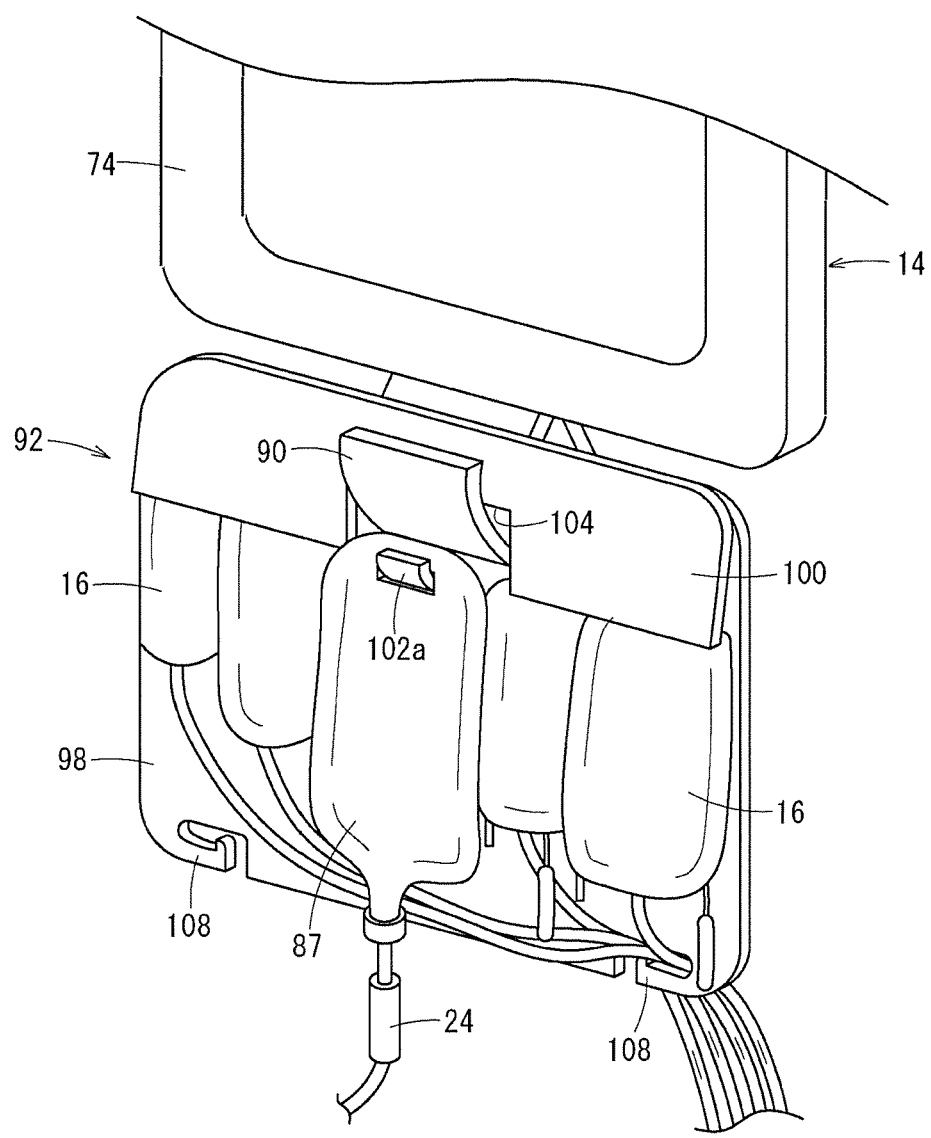
FIG. 3 is a view of the medical bag hanger hung on a hook provided in a centrifugal device.

The anticoagulant introduction unit 24 is connectable to an ACD solution storage bag 87 (see FIG. 3). In using the blood sampling line set 12, an ACD solution or an anticoagulant is supplied, as an initial operation, from the ACD solution storage bag 87 to the channel 18 through the anticoagulant introduction unit 24 so as to prevent coagulation of the whole blood.

In blood component sampling using the blood sampling line set 12, the whole blood taken from the donor through the blood sampling needle 25 flows, from one end 18*a* to which the introduction tube 46 is connected, into the first chamber 40 of the channel 18 mounted on the mounting groove 86. The inflowing whole blood flows toward the other end 18*b* along an extension direction of the channel 18. While flowing, the whole blood is separated by centrifugal force associated with rotation of the rotor 78. In this embodiment, the whole blood is separated by centrifugation into plasma (platelet-poor plasma: PPP) or a blood component having light specific weight (supernatant component), concentrated red cells or a blood component having heavy specific weight (sedimentation component), and buffy coat (BC) or a blood component having medium specific weight.

First to third lead-out tubes 48*a* to 48*c* are connected to the other end 18*b* of the channel 18.

The first lead-out tube 48*a* is connected to a reservoir 50 provided inside the cassette 22. The concentrated red cells generated by centrifugation of the first chamber 40 are led to the reservoir 50 by the first lead-out tube 48*a*.

The second lead-out tube 48*b* is connected through the cassette 22 to a tube 52 connected to the bag for PPP 30 and the reservoir 50 provided inside the cassette 22. The plasma generated in the first chamber 40 by centrifugation of the whole blood is led to the cassette 22 through the second lead-out tube 48*b*, and part of the plasma is introduced into the bag for PPP 30 through the tube 52, and the rest of the plasma is introduced into the reservoir 50. The blood components (concentrated red cells and plasma) stored in the reservoir 50 are led out to the blood sampling/blood returning unit 26 after centrifugation and returned to the donor through the blood sampling needle 25.

The third lead-out tube 48*c* is connected to a concentrator 56 serving as a secondary separator having a second chamber 54. The buffy coat generated in the first chamber 40 by centrifugation of the whole blood is introduced into the concentrator 56 by the third lead-out tube 48*c*. Buffy coat contains a blood component of white blood cells and platelet-rich plasma (a platelet-containing component).

The concentrator 56 introduces the buffy coat from the channel 18 into the second chamber 54 and further centrifugally separates the buffy coat by centrifugal force associated with the rotation of the rotor 78. The concentrator 56 is formed in a conical shape with a plurality of steps. When the concentrator 56 is attached to the rotor 78, the vertex of the conical shape is disposed far from the centrifugal axis, and the base of the conical shape is disposed close to the centrifugal axis.

In the concentrator 56, the buffy coat is separated into white blood cells or a blood component having heavy specific weight, and platelets or a blood component having light specific weight (specifically, a platelet-containing component including plasma and platelets). The white blood cells are captured by the plurality of steps formed in the concentrator 56. The platelets flow out to a relay tube 58 connected to an outlet (bottom side) of the concentrator 56 and are introduced into the bag for platelet 34 through the cassette 22 and the tube 60. With introduction of the platelets, a platelet additive solution (PAS) is supplied to the bag for platelet 34 from the bag for platelet additive solution 32 through the tube 62, the cassette 22, and the tube 60.

It should be noted that the introduction tube 46, the first lead-out tube 48*a*, the second lead-out tube 48*b*, and the relay tube 58 are bundled by a bundling sheath 64. In this embodiment, the fluid delivery line 17 includes the introduction tube 46, the first to third lead-out tubes 48*a* to 48*c*, the concentrator 56, and the relay tube 58. Hereinafter, a part of the blood sampling line set 12 that includes the channel 18 and the fluid delivery line 17 is referred to as a "channel set 36".

The centrifugal device 14 is repeatedly used in blood component sampling and provided in, for example, a medical facility, and a vehicle for blood sampling. The centrifugal device 14 includes a box-like apparatus main body 70 having a relatively long length in a height direction; a monitor 74 supported by a support rod 88 projecting upward from the upper back of the apparatus main body 70; an attachment unit 76 that allows the cassette 22 of the blood sampling line set 12 to be attached thereto; a centrifugal unit 72 housed in the apparatus main body 70; and a door 81 that opens or closes the front side of the apparatus main body 70.

The apparatus main body 70 is configured to house the plurality of bags 16 of the blood sampling line set 12 inside or hold the same outside and configured to control centrifugation of blood taken into the blood sampling line set 12.

The monitor 74 is of a touch panel type and serves as a display unit that displays operating states and the like of the apparatus main body 70 when centrifuging blood and doubles as an input unit for inputting instructions to operate the apparatus main body 70. A hook 90 is provided near a lower part of the monitor 74. Specifically, the hook 90 is provided on the front side close to an upper end of the support rod 88 that supports the monitor 74. This hook 90 is placed within arm's reach of a small person.

The attachment unit 76 is disposed on the upper side of the apparatus main body 70, being configured to fit and hold the cassette 22. Although not illustrated in detail, the attachment unit 76 includes a plurality of pumps, a plurality of clamps, and a plurality of sensors. With attachment of the cassette 22 to the attachment unit 76, these pumps, clamps, and sensors are disposed on a path formed by the tubes 20 and the cassette 22 of the blood sampling line set 12.

The centrifugal unit 72 includes the rotor 78 that is rotatable about a vertical axis, and a drive unit 80 (motor) that drives the rotor 78 to rotate. The rotor 78 has an upper rotor 82 on which the channel 18 is mountable, and a lower rotor 84 that is rotatable coaxially with the upper rotor 82. The upper rotor 82 is rotatable relative to the lower rotor 84, and the upper surface 82a of the upper rotor 82 is provided with the mounting groove 86 to allow the channel 18 to be mounted.

The lower rotor 84 is connected to an output shaft of the drive unit 80. The upper rotor 82 and the lower rotor 84 are connected by a pinion assembly 85 in order to rotate the upper rotor 82 at twice the speed of the lower rotor 84. The pinion assembly 85 includes, for example, an intermediate gear supported on the lower rotor 84 so as to be rotatable about an axis perpendicular to the rotation axis a of the rotor 78, a lower gear that meshes with a lower part of the intermediate gear provided at a non-rotatable portion, and an upper gear provided on the upper rotor 82 about the rotation axis a.

With such a pinion assembly 85, the upper rotor 82 rotates twice each time the lower rotor 84 rotates. Accordingly, even when the channel 18 is continuously rotated by the rotor 78 for centrifugation, the extent of twist between the channel 18 and the plurality of tubes (such as the introduction tube 46) connected to the channel 18 falls within a predetermined range. Therefore, a rotary seal between the channel 18 and the plurality of tubes is not required.

A unit for rotating the upper rotor 82 at twice the speed of the lower rotor 84 is not limited to the pinion assembly 85, and other configurations may also be employed. For example, the upper rotor 82 and the lower rotor 84 may be rotated with separate motors so as to rotate the upper rotor 82 at twice the speed of the lower rotor 84.

Figure 2:
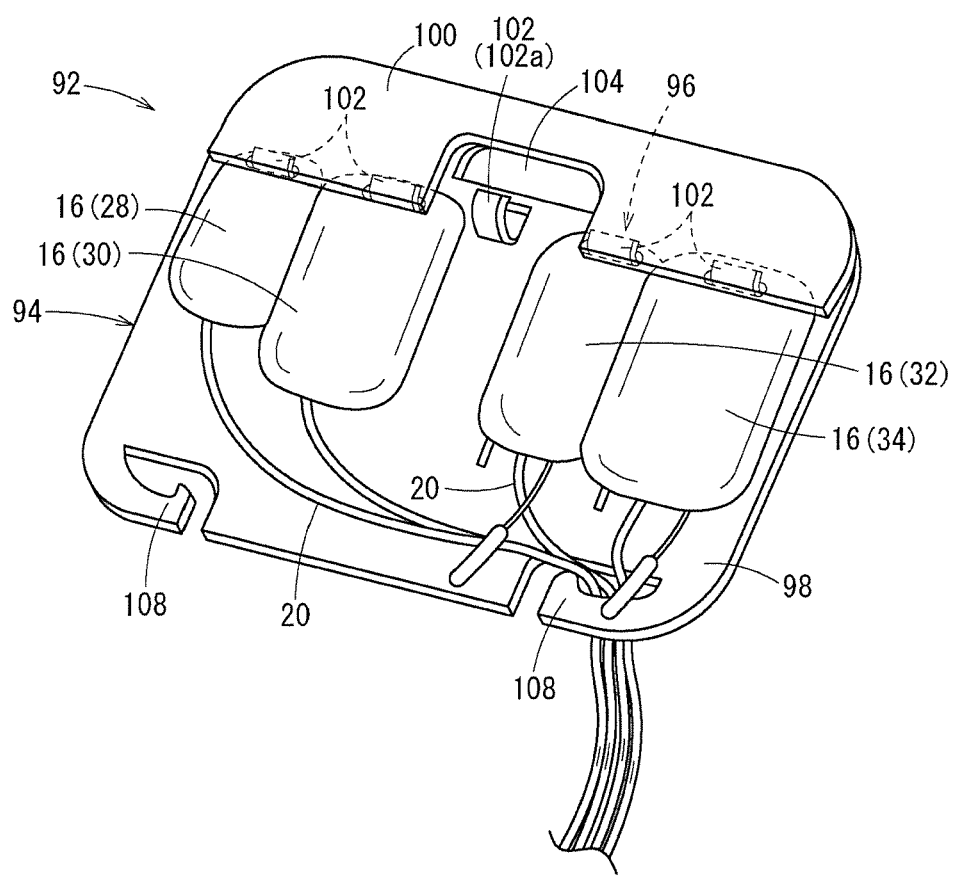
FIG. 2 is a perspective view of a medical bag hanger according to an embodiment of the present invention.

In FIG. 2, the plurality of bags 16 is attached to a medical bag hanger 92 (hereinafter simply referred to as the "hanger 92") according to the embodiment of the present invention. This hanger 92 is an instrument combined with the blood sampling line set 12 from the start. In other words, in an initial state (state of product offering) of the blood sampling line set 12, the plurality of bags 16 is preliminarily attached to the hanger 92.

Specifically, the hanger 92 includes a hanger main body 94 hangable on the centrifugal device 14, and a hook unit 96 provided to the hanger main body 94. The hanger main body 94 is provided with a plate-like or sheet-like base plate 98 including a hard material, and a cover 100 that covers an upper part of the base plate 98. The base plate 98 has such a size that the plurality of bags 16 is arranged side by side in the lateral direction. In this embodiment, the base plate 98 is formed into a horizontally elongated rectangular shape in plan view with round corners.

The hook unit 96 is provided on the upper part of the base plate 98. In this embodiment, the hook unit 96 includes a plurality of hooks 102 on which the plurality of bags 16 is hooked respectively and from which the plurality of bags 16 is individually detached. The plurality of hooks 102 is disposed at intervals in the lateral direction (in a longitudinal direction of the rectangular base plate 98) and projects to the front of the base plate 98. Furthermore, in this embodiment, one hook 102 (a central hook 102a) of the plurality of hooks 102 is for hooking and hanging the ACD solution storage bag 87 (see FIG. 3).

At the center of the upper part of the base plate 98, a hooking hole 104 is provided. As illustrated in FIG. 3, as the hooking hole 104 is hooked on the hook 90 provided in the centrifugal device 14, the hanger 92 is hung on the centrifugal device 14. Furthermore, as illustrated in FIG. 2, a fastening hook 108 is provided in each of the lower left and lower right of the base plate 98 so that the tubes 20 extending from the bags 16 are fastened in a bundle.

It should be noted that the number and arrangement of the fastening hooks 108 are not limited to the example illustrated in the drawing. For example, the fastening hooks 108 may be provided in one of the lower left or lower right of the base plate 98. Alternatively, one fastening hook 108 may be provided in (or near) the middle of a lower part of the base plate 98.

Figure 4:
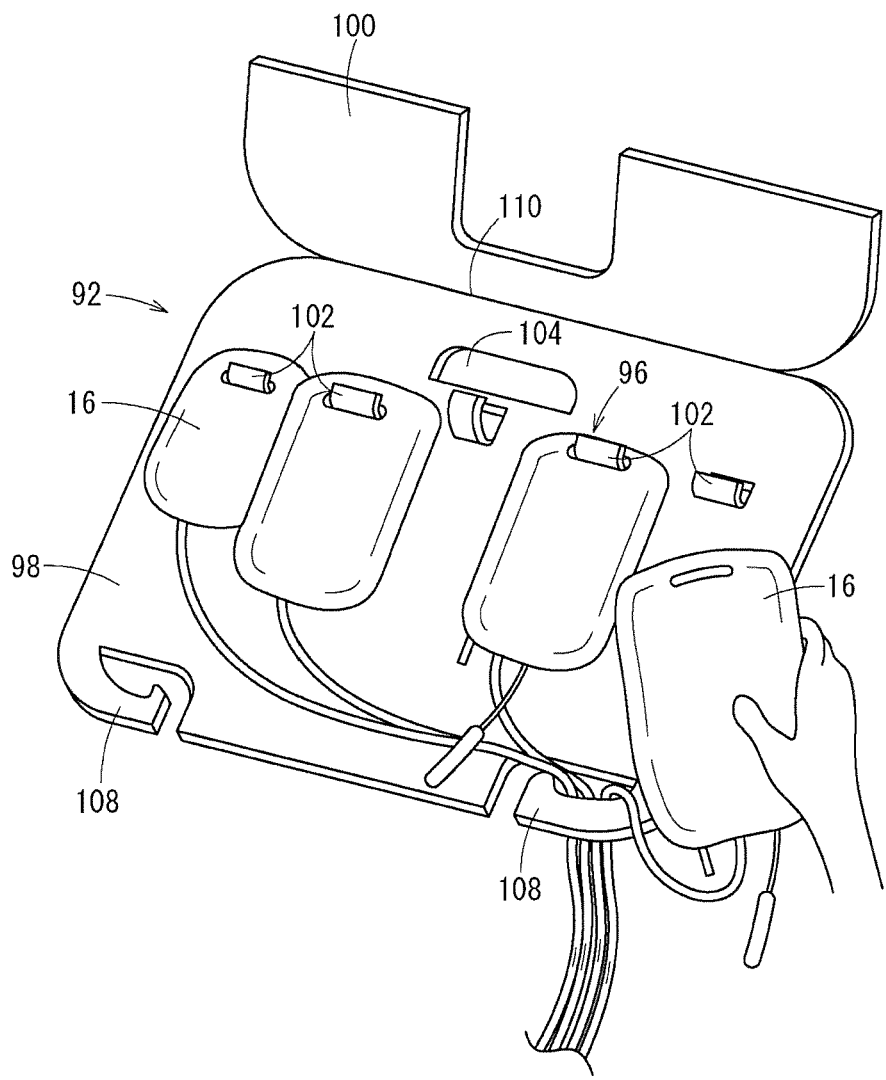
FIG. 4 is a view illustrating how a bag is detached from the medical bag hanger.

The cover 100 is formed in a plate-like or sheet-like shape and configured to cover an upper surface of the base plate 98 and the hook unit 96 in the initial state. As illustrated in FIG. 4, when the cover 100 is opened, the plurality of bags 16 is individually detached from the hook unit 96. Specifically, the cover 100 is connected to an upper edge of the base plate 98, involving a hinge 110.

In this embodiment, the hinge 110 is a thin portion formed thinner than the base plate 98 and the cover 100. The hinge 110 may have a structure in which the cover 100 is rotatably connected to the base plate 98 by a shaft member.

Such a hanger 92 preferably includes a hard material such as plastic (for example, polypropylene, and polycarbonate).

Hereinafter described is the function effect of the hanger 92 according to this embodiment having the above configuration.

The blood sampling line set 12 is mounted on the centrifugal device 14 in order to prepare (set up) for sampling blood components from a donor with the blood sampling system 10 illustrated in FIG. 1. In mounting the blood sampling line set 12 on the centrifugal device 14, specifically, the cassette 22 is attached to the attachment unit 76, and the plurality of bags 16 is hung on the centrifugal device 14, and the channel 18 is mounted on the rotor 78.

In this case, according to the hanger 92 according to this embodiment, the plurality of bags 16 included in the blood sampling line set 12 is assembled in advance. Therefore, in use, as illustrated in FIG. 3, with simple operation of hanging the hanger 92 on the hook 90 provided in the centrifugal device 14, the plurality of bags 16 is easily attached to the centrifugal device 14. Furthermore, the hook 90 is provided in the centrifugal device 14 at a position within arm's reach of a small worker so that the worker is able to detach the plurality of bags 16 without difficulty.

In this embodiment, the ACD solution storage bag 87 is not included in the blood sampling line set 12, but the hanger 92 is also provided with the hook 102a for the ACD solution storage bag 87. Therefore, as illustrated in FIG. 3, the ACD solution storage bag 87 is hookable on the hook 102a of the hanger 92 later. The anticoagulant introduction unit 24 is connected to a port of the ACD solution storage bag 87.

In this embodiment, the hanger main body 94 includes the base plate 98 including a hard material and provided with the hook unit 96, and the plurality of bags 16 is arranged side by side on the surface of the base plate 98. With this configuration, inside the package that houses the blood sampling line set 12, the tubes and the like in the blood sampling line set 12 are housed in the back of the base plate 98 so that the bags 16 are prevented from being tracked by the tubes and the like.

In this embodiment, the cover 100 covers the upper surface of the base plate 98 and the hook unit 96 in the initial state, and when the cover 100 is opened, the plurality of bags 16 is detachable from the hook unit 96. With this configuration, the cover 100 is closed in the initial state so that the bags 16 do not unintentionally come off the hanger 92 when the hanger 92 is hung on the centrifugal device 14. Furthermore, after blood treatment, when the cover 100 is opened as illustrated in FIG. 4, the hook unit 96 is exposed so that the plurality of bags 16 is detachable from the hanger 92 with ease.

In this embodiment, the hook unit 96 includes the plurality of hooks 102 so that the plurality of bags 16 is easily handled after blood sampling.

In this embodiment, the hanger main body 94 includes the fastening hooks 108 configured to fasten the plurality of tubes 20 in a bundle so that the plurality of tubes 20 is assembled, which simplifies attachment of other parts of the blood sampling line set 12.

Hereinafter described is several embodiments of the blood sampling device package provided with the blood sampling line set 12, the hanger 92, and a package main body that houses these members.

Figure 5:
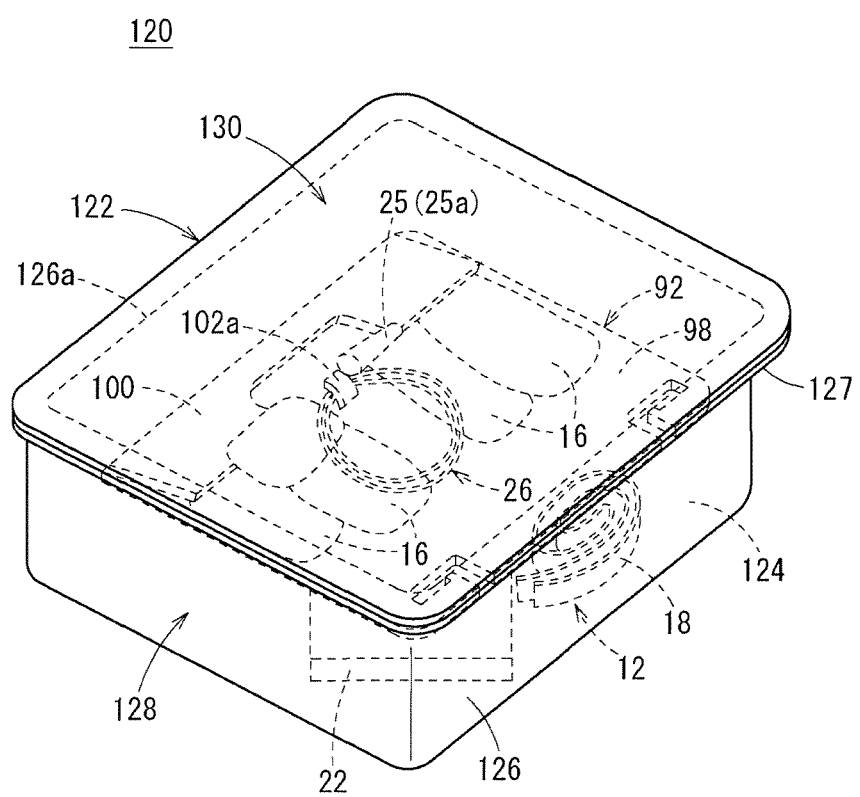
FIG. 5 is a perspective view of a blood sampling device package according to a first embodiment of the present invention.

In FIG. 5, the blood sampling device package 120 according to a first embodiment of the present invention includes the blood sampling line set 12, the hanger 92 to which the plurality of bags 16 is attached, and a package main body 122 that houses the blood sampling line set 12 and the hanger 92. The blood sampling line set 12 is offered to a user as being housed in the package main body 122 together with the hanger 92 in this manner.

The package main body 122 includes a chassis 128 having a box-like shape provided with a bottom wall 124 and a peripheral wall 126, and a lid member 130 joined to an upper end of the peripheral wall 126 of the chassis 128. The bottom wall 124 has a substantially flat quadrilateral shape. The peripheral wall 126 projects upward from a peripheral edge of the bottom wall 124, and an opening 126a is formed inside an upper end of the peripheral wall 126. A flange 127 projects outward from the upper end of the peripheral wall 126. The chassis 128 includes a relatively hard material (for example, polypropylene, and polycarbonate). In addition, the chassis 128 preferably includes a transparent material.

Figure 6:
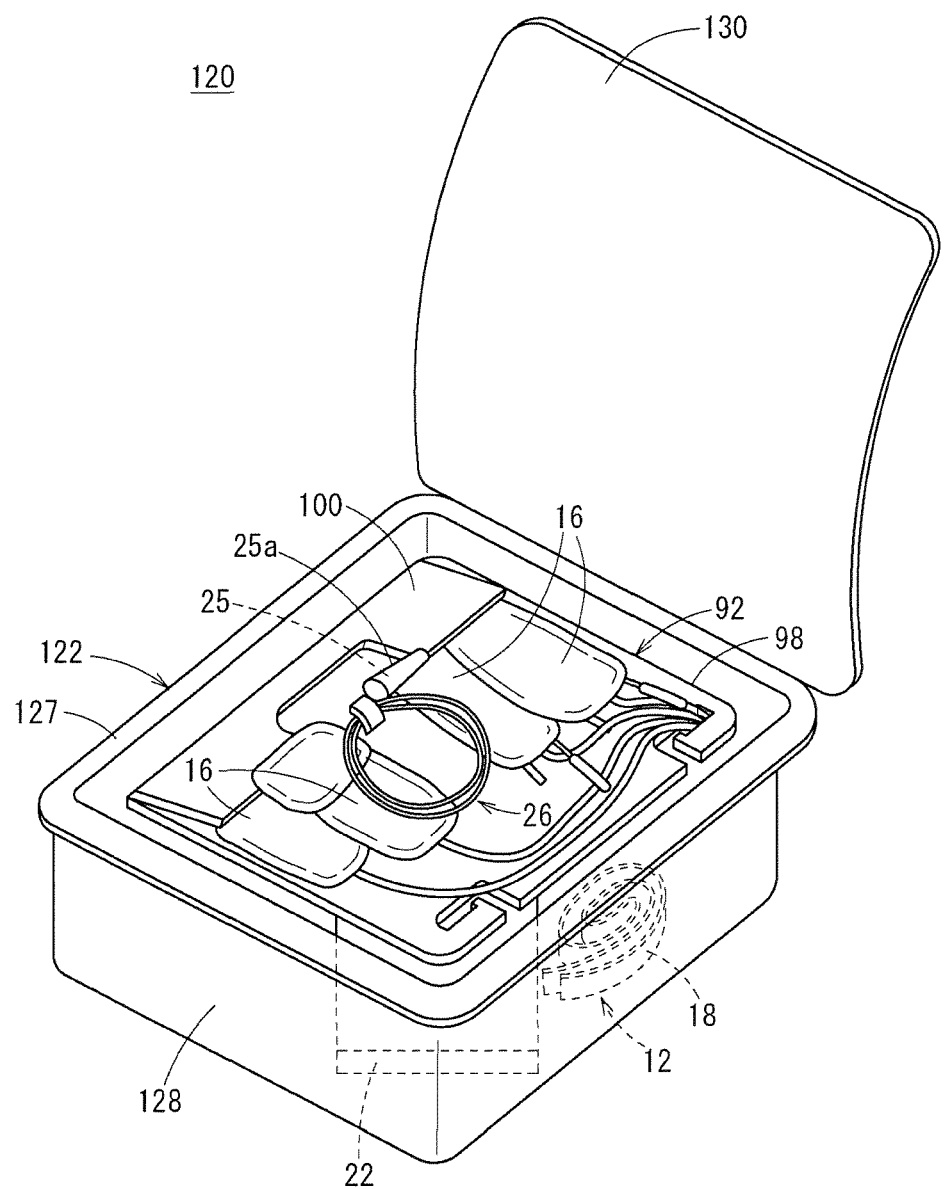
FIG. 6 is a perspective view of the blood sampling device package illustrated in FIG. 5 being opened.

The lid member 130 is a flexible sheet-like member peelably joined to an upper surface of the flange 127 by, for example, heat seal. Therefore, in using the blood sampling line set 12, as illustrated in FIG. 6, the lid member 130 is peeled off the flange 127 to open the package main body 122 so that the blood sampling line set 12 is easily taken out.

As illustrated in FIG. 5, the medical bag hanger 92 is placed on the cassette 22 and the channel 18 inside the package main body 122 in the initial state (before opened). Specifically, the hanger 92 is placed on the cassette 22 and the channel 18, while the side on which the plurality of bags 16 is arranged faces upward. Therefore, most of the tubes in the blood sampling line set 12 are housed under the hanger 92.

In this embodiment, as illustrated in FIG. 5, the blood sampling/blood returning unit 26 including the blood sampling needle 25 and the like is hooked and attached to the hook 102a provided in the hanger 92 (the hook for the ACD solution storage bag 87) inside the package main body 122 in the initial state. Therefore, the blood sampling/blood returning unit 26 is placed on the hanger 92. In FIG. 5, it should be noted that a cap 25a is fitted in the blood sampling needle 25 (similar in FIGS. 6 and 11).

Hereinafter described is the function effect of the blood sampling device package 120 according to this embodiment having the above configuration.

In using the blood sampling device package 120, as illustrated in FIG. 6, the lid member 130 is peeled off the chassis 128 so that the blood sampling line set 12 housed inside the chassis 128 is exposed. In other words, the blood sampling device package 120 is opened. When taking the blood sampling line set 12 out of the package main body 122, the hanger 92 to which the plurality of bags 16 is attached is taken out as a first step, then, the cassette 22 is taken out as a second step, and the channel 18 is taken out as a third step. Accordingly, the attachment procedure is easy to follow, which enables a worker to easily attach the blood sampling line set 12 to the centrifugal device 14.

Figure 7:
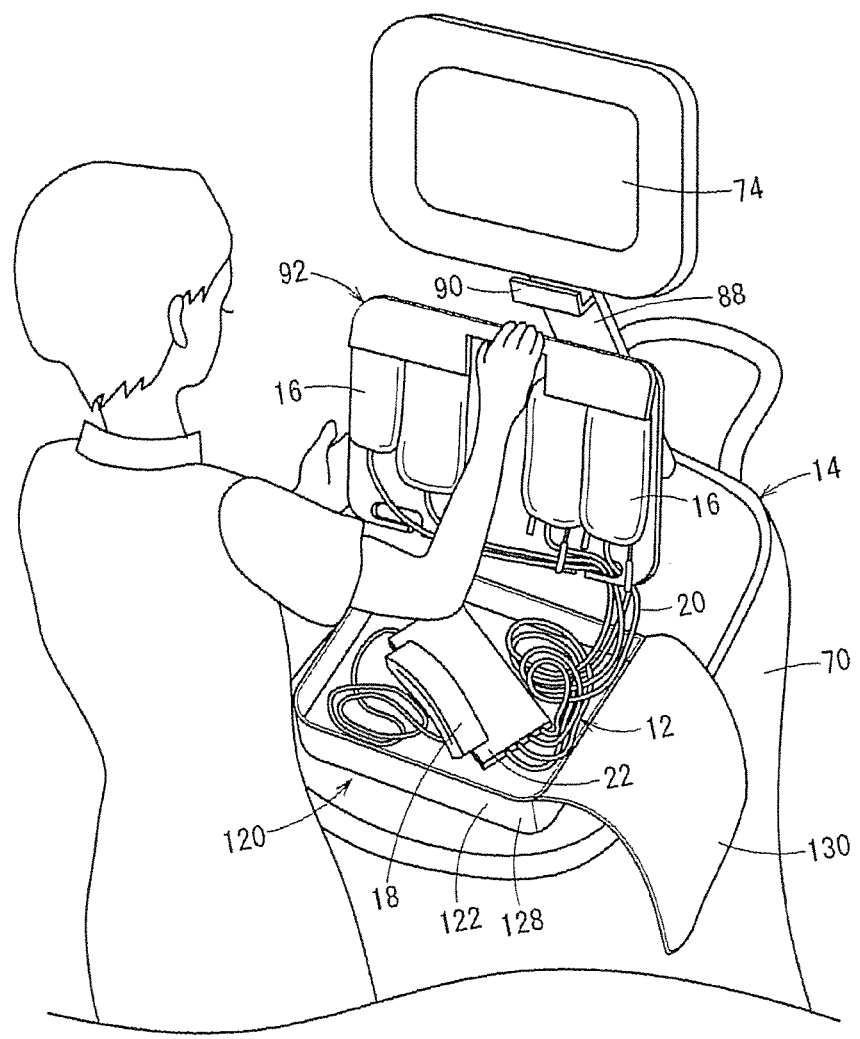
FIG. 7 is a view for explaining a method of taking out a blood sampling line set from the blood sampling device package illustrated in FIG. 5.

In this case, for example, as illustrated in FIG. 7, the blood sampling device package 120 is placed on an upper surface of the apparatus main body 70 of the centrifugal device 14 and opened, and then, the blood sampling line set 12 is taken out. More specifically, as the first step, the hanger 92 with the plurality of bags 16 attached thereto is taken out of the chassis 128 and hooked on the hook 90 provided in the centrifugal device 14 so that the hanger 92 is hung. Although not illustrated in FIG. 7, the blood sampling/blood returning unit 26 herein is hooked on the hook unit 96 of the hanger 92 (see FIGS. 5 and 6) so that the blood sampling/blood returning unit 26 is also temporarily attached to the centrifugal device 14 through the hanger 92. For this reason, in the next operation, the cassette 22 and the channel 18 are taken out without being disrupted by the blood sampling/blood returning unit 26.

Next, as the second step, the cassette 22 is taken out of the chassis 128, and the cassette 22 is mounted on the attachment unit 76 of the centrifugal device 14. In this case, if the package main body 122 is in the way of operation, the cassette 22 may be mounted on the attachment unit 76 after moving the package main body 122 to another place from the upper surface of the apparatus main body 70.

Figure 8:
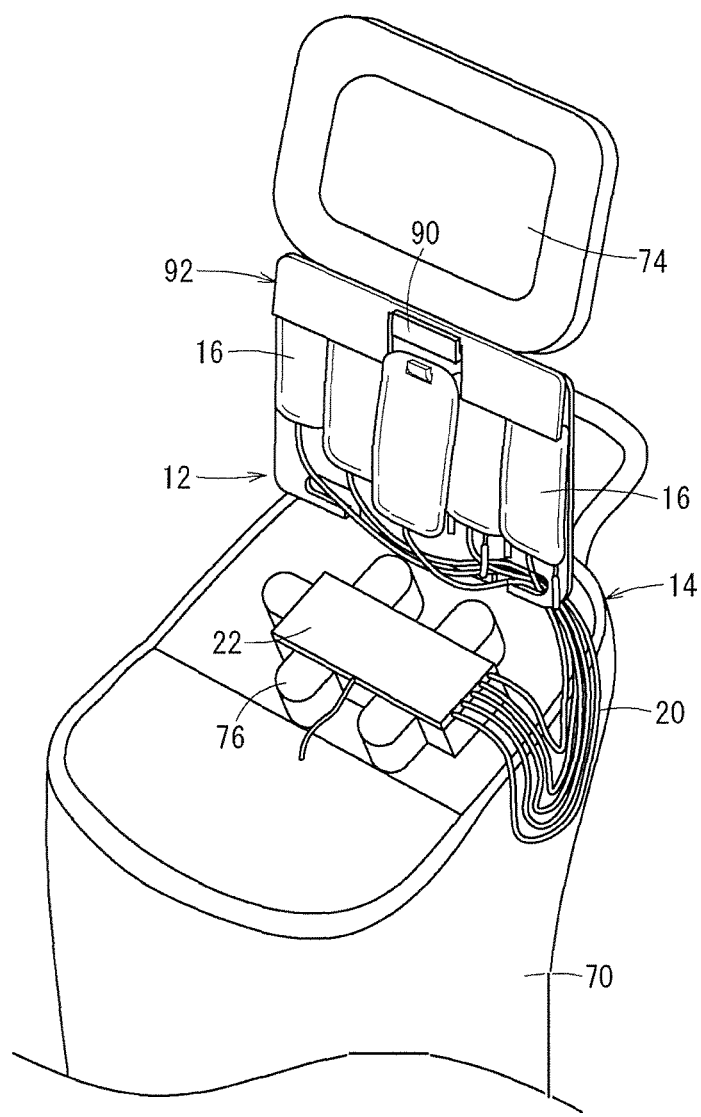
FIG. 8 is a view showing the blood sampling line set being mounted on the centrifugal device.

Next, as the third step, the channel 18 is taken out of the chassis 128 and mounted on the rotor 78 (see FIG. 1) provided in the apparatus main body 70. Accordingly, as illustrated in FIG. 8, the blood sampling line set 12 is attached to the centrifugal device 14.

In this manner, according to the blood sampling device package 120 of this embodiment, when the blood sampling device package 120 is placed on the apparatus main body 70 of the centrifugal device 14 and the blood sampling device package 120 is opened on the apparatus main body 70 to take out the blood sampling line set 12, following the aforementioned procedure (first to third steps) makes it possible to attach the blood sampling line set 12 to the centrifugal device 14 smoothly.

When the size of the hanger 92 is large, the hanger 92 may be foldable in half, and the hanger 92 may be housed inside the package main body 122 as being folded. Accordingly, even when the size of the hanger 92 is large, it is possible to downsize the blood sampling device package 120.

Figure 9:
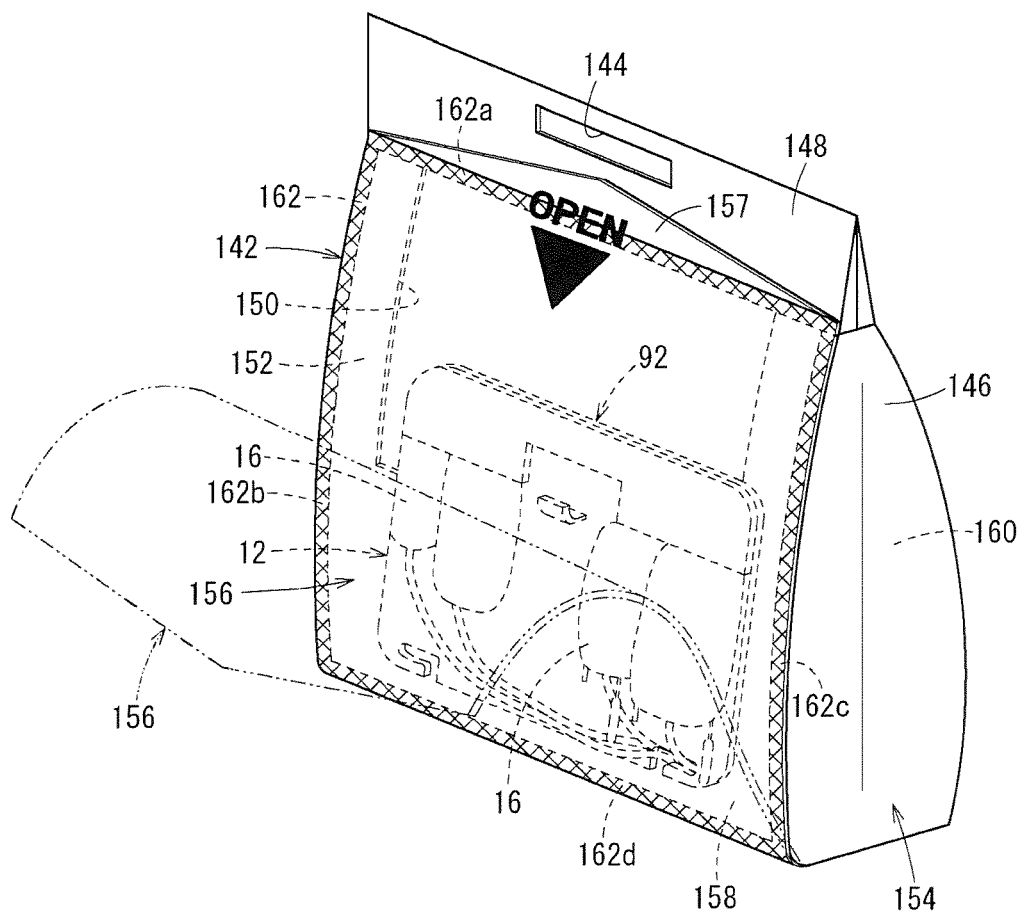
FIG. 9 is a perspective view of a blood sampling device package according to a second embodiment of the present invention.

In FIG. 9, the blood sampling device package 140 according to a second embodiment of the present invention includes the blood sampling line set 12, the hanger 92 to which the plurality of bags 16 is attached, and a package main body 142 that houses the blood sampling line set 12 and the hanger 92. The blood sampling line set 12 is offered to a user as being housed in the package main body 142 together with the hanger 92 in this manner.

Figure 12:
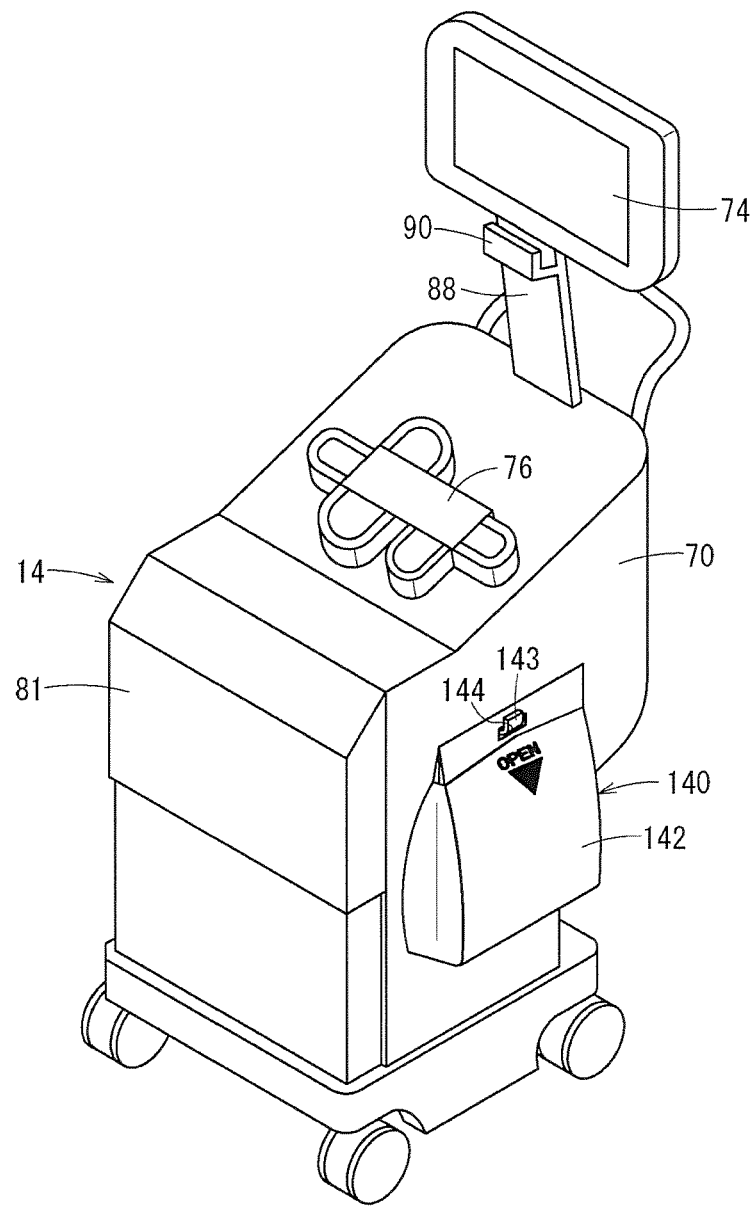
FIG. 12 is a perspective view of the blood sampling device package illustrated in FIG. 9 being hung on a side surface of the centrifugal device.

The package main body 142 is hookable and hangable on a side surface of the centrifugal device 14. Specifically, a hanging hole 144 is provided in an upper part of the package main body 142, and as illustrated in FIG. 12, the hanging hole 144 is hooked on a hook 143 provided on the side surface of the centrifugal device 14 so that the package main body 142 is hangable on the side surface of the centrifugal device 14.

In FIG. 9, the package main body 142 includes a bag unit 146 that houses the blood sampling line set 12 and an upper end member 148 attached to an upper end of the bag unit 146. The bag unit 146 has a plurality of housing rooms communicating with each other through an opening 150, and components of the blood sampling line set 12 are separately housed in the plurality of housing rooms.

Figure 10:
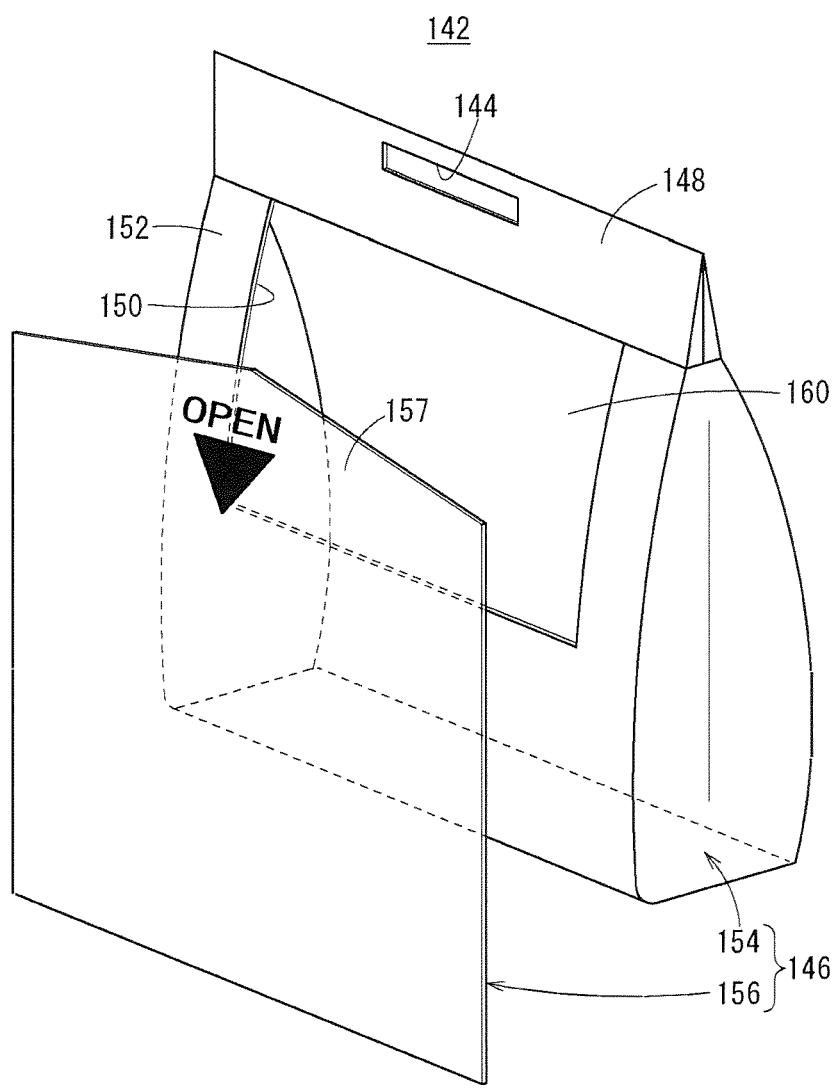
FIG. 10 is an exploded perspective view of a package main body.

Specifically, as illustrated in FIGS. 9 and 10, the bag unit 146 includes a bag main body 154 provided with the opening 150 in a front wall 152 of the bag unit 146, and a cover sheet member 156 that covers the opening 150. At least a part of the cover sheet member 156 is peelably attached to the front wall 152 of the bag main body 154.

Figure 11:
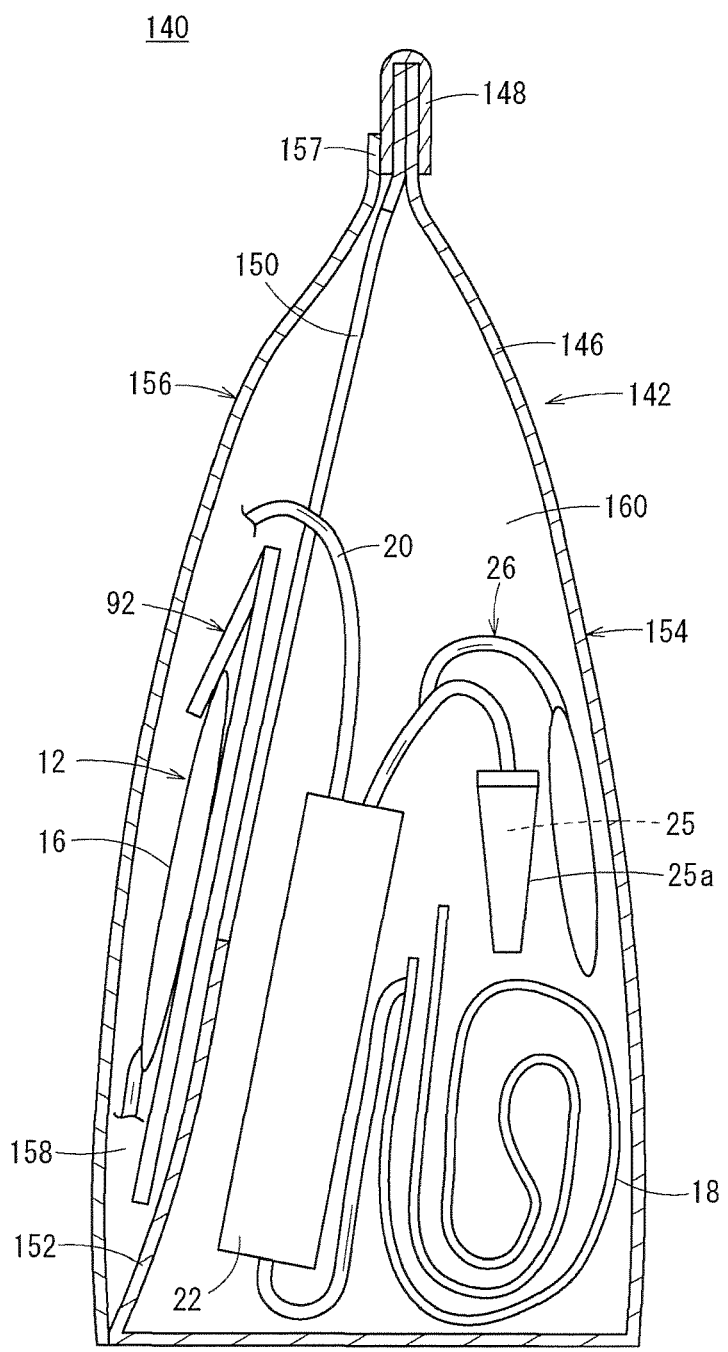
FIG. 11 is a schematic cross-sectional view for explaining a state in which a blood sampling line set is stored in the blood sampling device package illustrated in FIG. 9.

As illustrated in FIG. 11, the plurality of housing rooms includes a first housing room 158 formed between the front wall 152 of the bag main body 154 and the cover sheet member 156, and a second housing room 160 formed inside the bag main body 154. The hanger 92 is housed in the first housing room 158, and the cassette 22, the channel 18, and the blood sampling/blood returning unit 26 are housed in the second housing room 160. In the second housing room 160, the cassette 22 is housed in front of the channel 18 and the blood sampling/blood returning unit 26.

The bag main body 154 is formed in a sac-like shape, including a flexible resin material. The bag main body 154 illustrated herein is formed to have the shallow upper side and the deep lower side. The opening 150 of the bag main body 154 is formed relatively large from a central part to an upper part in a height direction of the bag main body 154 so that the cassette 22, the channel 18, and the blood sampling/ blood returning unit 26 are easily taken out of the bag main body 154. The front wall 152 of the bag main body 154 is included in a partition wall that partitions the first housing room 158 and the second housing room 160.

The cover sheet member 156 is formed in a sheet-like shape, including a material similar to that of the bag main body 154. The cover sheet member 156 is peelably joined to the bag main body 154 and the upper end member 148 in a part near a peripheral edge of the cover sheet member 156. In this embodiment, the cover sheet member 156 is peelably joined to the bag main body 154 and the upper end member 148 by heat seal. In FIG. 9, a sealed portion 162 (a cross hatched portion) formed by heat seal makes a circuit in a quadrilateral shape in a front view substantially along the peripheral edge of the cover sheet member 156.

An upper end 157 of the cover sheet member 156 is formed in a triangular shape, and one side 162*a* of the quadrangular sealed portion 162 corresponds to the base of the triangular shape. Accordingly, the upper end 157 of the cover sheet member 156 is easily torn off. The remaining three sides 162*b* to 162*d* of the sealed portion 162 join left, right, and lower edges of the front wall 152 of the bag main body 154 and left, right, and lower edges of the cover sheet member 156.

It should be noted that an upper end of the opening 150 may be lowered from the position illustrated in FIG. 10 so that the front wall 152 remains at a position under the upper end member 148 in the upper part of the bag main body 154, and one side 162*a* of the sealed portion 162 may be formed at the portion.

The cover sheet member 156 is not necessarily completely separated from the bag main body 154. The sealed portion 162 may be formed in such a manner that the opening 150 and the hanger 92 are exposed with at least a part of the cover sheet member 156 being peeled off the bag main body 154. Therefore, for example, in place of the lower side 162*d* of the sealed portion 162, a non-peelable fixed portion may be formed so that the lower edge of the cover sheet member 156 is non-peelably fixed to the bag main body 154.

It should be noted that the bag main body 154 and the cover sheet member 156 preferably include a transparent material.

Hereinafter described is the function effect of the blood sampling device package 140 according to this embodiment having the above configuration.

As illustrated in FIG. 12, the blood sampling device package 140 is hookable on the side surface of the centrifugal device 14. With this configuration, the blood sampling device package 140 is prepared in a space-saving manner within arm's reach of a worker.

In using the blood sampling device package 140, the cover sheet member 156 is peeled off the bag main body 154 to expose the hanger 92 and the opening 150, as illustrated by an imaginary line in FIG. 9. In other words, the blood sampling device package 140 is opened. In opening the blood sampling device package 140, it should be noted that the cover sheet member 156 is easily peeled off by pinching and pulling the upper end 157 of the cover sheet member 156.

In this case, the bag unit 146 of the package main body 142 has the plurality of housing rooms communicating with each other through the opening 150, and components of the blood sampling line set 12 are separately housed in the plurality of housing rooms. With this configuration, when attaching the blood sampling line set 12 to the centrifugal device 14, the components of the blood sampling line set 12 are taken in order out of the plurality of housing rooms of the bag unit 146, which leads to efficient attachment operation.

Particularly, in this embodiment, the plurality of housing rooms includes the first housing room 158 formed between the front wall 152 of the bag main body 154 and the cover sheet member 156, and the second housing room 160 formed inside the bag main body 154. With this configuration, at first, at least a part of the cover sheet member 156 is peeled off the bag main body 154 so that a part of the blood sampling line set 12 is taken out of the first housing room 158, and then, the remaining components of the blood sampling line set 12 are taken out of the second housing room 160 through the opening 150. Therefore, the blood sampling device package 140 has a simple configuration so that the blood sampling line set 12 is easily taken out.

Particularly, in this embodiment, the medical bag hanger 92 to which the plurality of bags 16 is attached is housed in the first housing room 158, and the cassette 22, the channel 18, and the blood sampling needle 25 are housed in the second housing room 160, where the cassette 22 is housed in front of the channel 18 and the blood sampling needle 25 in the second housing room 160. With this configuration, when taking the blood sampling line set 12 out of the package main body 142, the hanger 92 to which the plurality of bags 16 is attached is taken out as a first step, the cassette 22 is taken out as a second step, and then, the channel 18 and the blood sampling needle 25 are taken out as a third step.

Accordingly, the attachment procedure is easy to follow, which enables a worker to easily attach the blood sampling line set 12 to the centrifugal device 14.

More specifically, in the first step, the hanger 92 with the plurality of bags 16 attached thereto is taken out of the first housing room 158 of the bag unit 146 hung on the side surface of the centrifugal device 14 and hooked on the hook 90 provided in the centrifugal device 14 so that the hanger 92 is hung. Next, in the second step, the cassette 22 is taken out of the second housing room 160, and the cassette 22 is mounted on the attachment unit 76 of the centrifugal device 14. Next, in the third step, the channel 18 and the blood sampling/blood returning unit 26 are taken out of the second housing room 160, and the channel 18 is mounted on the rotor 78 (see FIG. 1) provided in the apparatus main body 70.

The present invention is not limited to the aforementioned embodiments and may be modified in various manners without departing from the gist of the present invention.

The invention claimed is:

1. A bag hanging assembly, comprising:
a main body including a hook unit and a sheet-like base plate, the sheet-like base plate having a horizontally elongated rectangular shape; and
a plurality of bags,
wherein the main body is configured to be removably hung from an external surface of a blood component separation device, wherein the plurality of bags is configured to be hooked to the hook unit, and individual bags of the plurality of bags are arranged side by side on a surface of the sheet-like base plate when hooked to the hook unit, wherein the hook unit is provided on an upper surface of the sheet-like base plate, and
wherein the main body further includes a cover configured to cover the upper surface of the sheet-like base plate and the hook unit in an initial state, and to allow the plurality of bags to be detached from the hook unit when opened.

2. The bag hanging assembly of claim 1,
wherein the sheet-like base plate comprises a hole above the hook unit that enables the main body to be removably hung from the external surface of the blood component separation device.

3. The bag hanging assembly of claim 1, wherein the hook unit includes a plurality of hooks on which the plurality of bags is hooked, respectively, and from which the individual bags of the plurality of bags are detachable.

4. The bag hanging assembly of claim 3, wherein the main body further includes a hook configured to bundle and fasten a plurality of tubes of a blood sampling line set.

5. A blood sampling device package, comprising:
a blood sampling line set including a plurality of bags; and
a bag hanging assembly to which the plurality of bags is attached, the bag hanging assembly including a main body, the main body including a hook unit and a sheet-like base plate, the sheet-like base plate having a horizontally elongated rectangular shape,
wherein the sheet-like base plate comprises a hole above the hook unit that enables the main body to be removably hung from an external surface of a blood component separation device, wherein the plurality of bags is configured to be hooked to the hook unit, and individual bags of the plurality of bags are arranged side by side on a surface of the sheet-like base plate.

6. The blood sampling device package of claim 5, wherein the blood sampling line set and the bag hanging assembly are housed within a package main body of the blood sampling device package.

7. The blood sampling device package of claim 6, wherein the blood sampling line set further includes a cassette connected to the plurality of bags by a plurality of tubes, and a separator channel connected to the cassette by a fluid delivery line,
wherein the package main body includes a chassis having a box-like shape including a bottom wall and a peripheral wall, the peripheral wall including a lid member joined to an upper end thereof, and
wherein the bag hanging assembly is placed on the cassette and the separator channel inside the package main body in an initial state.

8. The blood sampling device package of claim 7, wherein the bag hanging assembly is configured to be foldable and is housed inside the package main body in a folded mode.

9. The blood sampling device package of claim 7, wherein the package main body is configured to hook to, and to hang from, a side surface of the blood component separation device.

10. The blood sampling device package of claim 9, wherein the package main body further includes a bag unit that houses the blood sampling line set,
wherein the bag unit includes a plurality of compartments in communication with each other, and
wherein the plurality of compartments separately house components of the blood sampling line set.

11. The blood sampling device package of claim 10, wherein the bag unit further includes a bag main body including an opening in a front wall thereof, and a cover sheet member configured to cover the opening, at least a part of the cover sheet member being peelably attached to the front wall of the bag main body, and
wherein the plurality of compartments includes a first compartment formed between the front wall of the bag main body and the cover sheet member, and a second compartment formed inside the bag main body.

12. The blood sampling device package of claim 11, wherein the cassette of the blood sampling line set is further connected to a blood sampling needle,
wherein the bag hanging assembly to which the plurality of bags is attached is housed in the first compartment, and
wherein the cassette, the separator channel, and the blood sampling needle are housed, such that the cassette is housed in front of the separator channel and the blood sampling needle, in the second compartment.

13. A blood sampling device package, the package comprising:
a blood sampling line set including a plurality of bags; and
a bag hanging assembly to which the plurality of bags is attached, the bag hanging assembly including a main body, the main body including a hook unit and a sheet-like base plate, the sheet-like base plate having a horizontally elongated rectangular shape,
wherein the sheet-like base plate comprises a hole above the hook unit that enables the main body to be removably hung from an external surface of a blood component separation device, wherein the plurality of bags is configured to be hooked to the hook unit, and individual bags of the plurality of bags are arranged side by side on a surface of the sheet-like base plate,
wherein an aspect of the blood sampling device package includes a sack-like shape.

14. The blood sampling device package of claim 13, wherein the blood sampling line set and the bag hanging assembly are housed within a bag main body of a bag unit of the blood sampling device package.

15. The blood sampling device package of claim 14, wherein the bag main body comprises a flexible resin material.

16. The blood sampling device package of claim 14, wherein the bag unit includes a plurality of compartments in communication with one another, and wherein components of the blood sampling line set are separately housed in the plurality of compartments.

17. The blood sampling device package of claim 16, wherein the bag main body includes an opening in a front wall thereof and a cover sheet member, and at least part of the cover sheet member is peelably attached to the front wall of the bag main body.

18. The blood sampling device package of claim 17, wherein the plurality of compartments includes a first compartment formed between the front wall of the bag main body and the cover sheet member, and a second compartment formed inside the bag main body.

19. The bag hanging assembly of claim 1, wherein the main body further includes a hook configured to bundle and fasten a plurality of tubes of a blood sampling line set.

* * * * *